Figure 1:
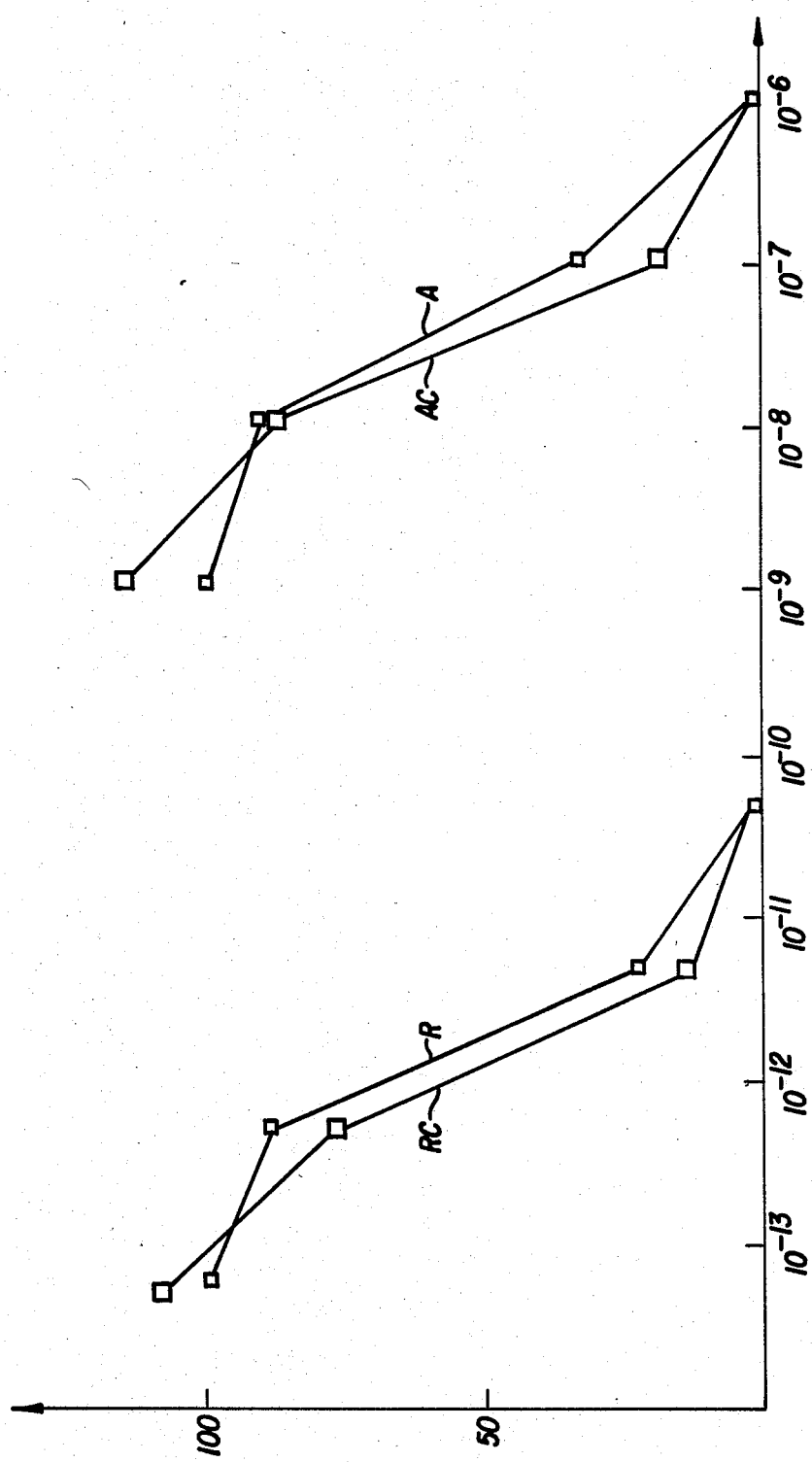

| United States Patent [19]
Jansen et al.

[11] Patent Number: 4,582,703
[45] Date of Patent: Apr. 15, 1986

[54] CYTOTOXIC MEDICAMENT FORMED FROM THE ASSOCIATION OF AT LEAST ONE IMMUNOTOXIN AND CHLOROQUIN

[75] Inventors: Franz Jansen, Assas; Pierre Gros, Montpellier, both of France

[73] Assignee: Sanofi, Paris, France

[21] Appl. No.: 552,052

[22] PCT Filed: Mar. 7, 1983

[86] PCT No.: PCT/FR83/00044
§ 371 Date: Oct. 21, 1983
§ 102(e) Date: Oct. 21, 1983

[87] PCT Pub. No.: WO83/03055
PCT Pub. Date: Sep. 15, 1983

[30] Foreign Application Priority Data

Mar. 10, 1982 [FR] France ................... 82 04047

[51] Int. Cl.$^4$ ............ A61K 39/00; A61K 37/00; A61K 39/44; C07G 7/00
[52] U.S. Cl. ................ 424/85; 260/112 B; 260/112 R; 514/2; 514/6; 424/88
[58] Field of Search ............ 424/85, 88, 177; 260/112 B, 112 R

[56] References Cited
PUBLICATIONS

Houston et al., *Cancer Res.*, vol. 41, pp. 3913–3917, Oct. 1981, "Cell-Specific Cytotoxicity Expressed by a Conjugate of Ricin and Murine Monoclonal Antibody Directed Against Thy 1.1 Antigen.

Ramakrishnan et al., *Science*, vol. 223, pp. 58–60, Jan. 6, 1984 "Inhibition of Human Acute Lymphoblastia Leukemia Cells by Immunotoxins: Potentiation by Chloroquine".

Leppla et al., *J. Biol. Chem.*, vol. 255(6), Mar. 25, 1980, pp. 2247–2250, "Inhibition of Diphtheria Toxin Degradation and Cytotoxic Action by Chloroquine".

Schneider et al., *Eur. J. Biochem.*, vol. 118(1), pp. 33–38, 1981, "Effect of Chloroquine and Methylamine on Endocytosis of Fluorescein–Labelled Control IgG and of Anti–Plasma Membrane . . . ".

Gilliland et al., *J. Biol. Chem.*, vol. 256(24), Dec. 25, 1981, pp. 12731–12739, "Characterization and Hybrid Molecules Containing Binding Subunit of Ricin Toxin".

*Primary Examiner*—Thomas G. Wiseman
*Assistant Examiner*—Robin Lyn Teskin
*Attorney, Agent, or Firm*—Stevens, Davis, Miller & Mosher

[57] ABSTRACT

The present invention relates to medicaments comprising, in association, at least one immunotoxin and chloroquin.

1 Claim, 3 Drawing Figures

CYTOTOXIC MEDICAMENT FORMED FROM THE ASSOCIATION OF AT LEAST ONE IMMUNOTOXIN AND CHLOROQUIN

The present invention relates to medicaments comprising, in association, at least one immunotoxin and chloroquin.

In prior French patent applications, bearing particularly Nos. 78 27 838, 79 24 655, 81 07 596 and 81 21 836, there is described the preparation of so called conjugated anticancer products obtained by coupling, by covalent bonding, the A chain of ricin with antibodies or antibody fragments directed against an antigen borne by a cell to be destroyed. The products of this type are denoted in the present application under the generic name of immunotoxins.

As set forth in French Patent Application No. 78 27 838, the conjugate is prepared by associating, by means of a covalent bond of the disulphide type, on the one hand, an immunoglobulin which is specific for a given antigen, or any fragment of this molecule which possesses the capacity of specific recognition with respect to the antigen, with, on the other hand, the A chain of ricin. The choice of a disulphide bond between the A chain and the immunoglobulin is based on the following arguments:

this type of bond is the type which exists in the natural ricin molecule, and it can be expected to be particularly suitable for presenting the A chain in a conformation which facilitates its penetration into the cell, while at best retaining its fundamental biological property of inhibiting protein synthesis;

this type of bond is biochemically labile, which provides the A chain, coupled in this way, with the possibility of being liberated from its carrier protein in the contents of the cell;

the A chain of ricin possesses a single cysteine residue in its structure and hence only one SH group capable of creating a disulphide bond. Consequently, the conjugates formed by involving this SH group in a disulphide bridge will be chemically well defined and will in no way modify the structure of the A chain, thus ensuring the integral retention of its biological activity; and there are efficient methods which make it possible to produce such a disulphide bond under conditions which are sufficiently mild to ensure the integrity of the biological properties of the protein constituents of the conjugates formed.

In order to produce such conjugates, the proteins to be coupled must each carry at least one sulphur atom which is naturally capable, or is artificially rendered capable, of creating the desired disulphide bond, whether these sulphur atoms already exist in the proteins or have been chemically introduced into these proteins. As indicated above, the A chain of ricin naturally possesses only one sulphur atom permitting the desired coupling. This is the sulphur atom in the thiol group of the single cysteine residue incorporated in the A chain. As regards the immunoglobulin or its fragments, several cases must be considered:

(1) In the case of an entire immunoglobulin, neither a free thiol group nor other sulphur atoms capable of being used for the coupling exist naturally in these proteins. It will therefore be necessary, in this case, to introduce one or more sulphur atoms into the immunoglobulin molecule artificially, so that:

the biological properties of the immunoglobulin are not profoundly impaired, and this sulphur atom, or these sulphur atoms, can subsequently be involved in the disulphide bond to be established with one or more molecules of the A chain of ricin.

(2) In the case of a Fab fragment, the situation is absolutely identical to that described above.

(3) If a fragment of the Fab' type is employed, it is possible to use the sulphur atom present in the free thiol group to carry out the coupling to the A chain. However, it is also possible to use the artificial introduction of one or more sulphur atoms; in this case, it is necessary to block the free thiol group in a stable manner beforehand, for example, by alkylation.

(4) Finally, if it is desired to couple a $F(ab')_2$ fragment of immunoglobulin, it is necessary, as in the case of the whole immunoglobulin, to introduce one or more sulphur-containing groups into $F(ab')_2$ artificially.

In all the cases in which one or more sulphur-containing radicals are introduced into the immunoglobulin or its fragments, it is necessary to avoid any substitution in the site for recognition of the antigen or in its immediate environment, which substitution could disturb the recognition properties of the antibody. In order to exclude this risk, the site for recognition of the antigen can be blocked temporarily, during the substitution reaction, by treating the antibody beforehand with the specific antigen, or with another antigen which possesses an adequate cross-reaction, or with a suitable hapten.

The operation for temporary protection can be carried out:

either in the liquid phase, if the antibody-antigen (or hapten) complex is soluble in the reaction medium; or in the heterogeneous phase, if this complex is spontaneously insoluble or, also, if it has been deliberately rendered insoluble by means of a suitable procedure, in particular by fixing the antigen (or hapten) to an insoluble support so that the modified support thus obtained possesses an adequate affinity for the antibody.

After the substitution step, it will be necessary to unblock the site for recognition of the antigen on the antibody by means of a suitable procedure for removing the antigen in order to regenerate the capacity of the antibody for specific recognition.

To produce the disulphide bridge between the two proteins, it is not possible to bring the two constituents of the conjugate, each carrying a SH group, into contact with one another and to carry out an oxidation. In fact, under these conditions, the coupling reaction is an equilibrium reaction which is very difficult to drive to completion. Furthermore, the desired reaction is accompanied by the formation of polymers of each of the two constituents, which would result in a very low yield of the desired product, and the presence of impurities which are very difficult to remove.

According to the invention, the conjugate is prepared by bringing one of the proteins, carrying its free SH group, into contact with the other protein, in which the SH group is activated by conversion into a mixed disulphide with a suitable sulphur-containing organic radical. The preparation of the conjugate can be represented by the equation:

$$P_1{-}SH + P_2{-}S{-}S{-}X \rightarrow P_1{-}S{-}S{-}P_2 + XSH$$

in which $P_1$ and $P_2$ represent the two proteins to be coupled and X denotes the activator radical. It is immediately apparent from this equation that, in each case, the coupling reaction can be carried out in accordance with two variants, depending on whether $P_1$ represents the immunoglobulin or its fragment and $P_2$ represents the A chain of ricin, or vice versa.

Case in Which $P_1$ Represents the Antibody or a Fragment and $P_2$ Represents the A Chain of Ricin To activate the free SH in the A chain of ricin, the solution of A chain, prepared as indicated above, is used, and it is subjected to an exchange reaction:

$$ASH + XSSX \rightarrow A-S-S-X + XSH \quad (1)$$

in which ASH represents the A chain of ricin and X represents the activator radical.

In particular, X can denote a pyrid-2- or -4-yl group which is optionally substituted by one or more alkyl or halogen radicals or carboxylic acid groups, or X can also represent a phenyl nucleus which is optionally substituted by one or more nitro or carboxylic acid groups. Reaction (1) is an equilibrium reaction, but the equilibrium can easily be displaced towards the right by using a large molar excess of the reagent XSSX, which is generally inexpensive and readily accessible. It is possible to monitor the course of reaction (1) by ultraviolet or visible spectrophotometry because the compound XSH which is formed shows an intense absorption in this region. When the reaction has reached the desired degree of completion, the excess of the reagent X—S—S—X, and also the reaction product X—SH, are removed by dialysis or filtration on a molecular sieve in gel form. Finally, a pure solution of the compound A—S—S—X in the chosen buffer is obtained. If necessary, this solution can be kept for several weeks after freezing.

The immunoglobulin substituted by a SH group is also prepared. To do this, the solution of immunoglobulin obtained above is used either as such or after blocking its site for the recognition of the antigen, with the corresponding hapten, followed by removal of the excess hapten. By reacting S-acetylmercaptosuccinic anhydride with this protein, it is possible to fix one or more S-acetylmercaptosuccinyl groups, per molecule of protein, by means of its free amino groups, and then to liberate the thiol groups by the action of hydroxylamine, as has been described (*Archives of Biochemistry and Biophysics*, 119, 41–49 (1967)). Dialysis makes it possible to remove the excess reagents and also the reaction products of low molecular weight.

All these operations are carried out in a phosphate buffer at pH=7.0 and at temperatures which do not exceed ambient temperature. The hapten which may have been used as a temporary blocking agent is removed from the solution finally obtained. If it proves necessary, this solution can be concentrated, for example, by ultrafiltration. The coupling between the two reagents thus prepared is effected by simple contact in aqueous solution, at ambient temperature, for a time varying from a few hours to one day, in accordance with the equation:

$$\text{Prot NH}-\text{CO}-\underset{\underset{\text{COO}^\ominus}{|}}{\underset{|}{\text{CH}}}-\text{SH} + A-S-S-X \longrightarrow \quad (4)$$

-continued
$$\text{Prot NHCOCH}-\text{S}-\text{S}-A + XSH$$
$$\underset{\underset{\text{COO}^\ominus}{|}}{\underset{|}{\text{CH}_2}}$$

The course of the reaction is followed by spectrophotometric determination of the compound XSH formed. The latter is removed by dialysis and a solution of the expected conjugate is obtained, which must be further purified. In fact, it is essential, in particular, to remove the molecules of A—S—S—X which have not reacted and which, if they were present in the conjugate, could give rise to a non-selective toxicity.

The purification can be effected by various known methods, such as fractional precipitation with the aid of water-miscible organic solvents or of salts, gel permeation chromatography, or also affinity chromatography on a column formed by an insoluble support on which the antigen (or the hapten) is fixed, against which antigen the antibody employed in the preparation of the conjugate is directed.

These purification methods can be applied directly to the dialysed solution originating from the coupling step. However, better results are obtained and, in particular, the subsequent formation of polymers of the conjugate is avoided by the prior blocking of the SH groups which remain free, with a reagent such as N-ethylmaleimide.

Case in Which $P_1$ Represents the A Chain of Ricin and $R_2$ Represents the Antibody In this case, the products required for the coupling are the A chain of ricin and the immunoglobulin (or its fragment), which is substituted by a group carrying one or more activated sulphur atoms. The A chain of ricin is used as obtained by the purification procedure described. The immunoglobulin substituted by an activated sulphur atom is prepared from the immunoglobulin itself by substitution with the aid of a reagent which itself carries an activated sulphur atom, in accordance with the equation:

$$\text{Prot} + Y-R-S-S-X \rightarrow \text{Prot}-R-SS-X$$

in which Prot denotes the immunoglobulin, Y represents a group permitting the covalent fixation of the reagent to the protein, R denotes a group which can simultaneously carry the substituents Y and —S—SX, and X denotes the activator radical.

A reaction of this type has already been used for coupling two proteins (identical or different) by means of a disulphide bridge, but the application of this principle to the coupling of an immunoglobulin with the A chain of ricin is new.

The functional group Y is a group which is capable of bonding in a covalent manner with any one of the groups carried by the side chains of the constituent aminoacids of the protein to be substituted. Among these latter groups, the terminal amino groups of lysyl radicals which are present in the protein are particularly indicated. In this case, Y can represent, in particular:

a carboxylic acid group which can bond to the amino groups of the protein in the presence of a coupling agent, such as a carbodiimide, and, in particular, a water-soluble derivative, such as 1-ethyl-3-(3-diethylaminopropyl)-carbodiimide;

a carboxylic acid chloride which is capable of reacting directly with the amino groups in order to acylate them;

a so-called "activated" ester, such as an ortho- or para-, nitro- or dinitro-phenyl ester, or also a N-hydroxysuccinimide ester, which reacts directly with the amino groups in order to acylate them;

an internal anhydride of a dicarboxylic acid, such as, for example, succinic anhydride, which reacts spontaneously with the amino groups in order to create amide bonds; or an iminoester group $$-C\begin{array}{c}\diagup NH \\ \diagdown OR_1\end{array},$$

in which $R_1$ is an alkyl group which reacts with the amino groups of the protein in accordance with the equation:

$$Prot-NH_2 + \begin{array}{c}HN\diagdown \\ \diagup \\ R_1O\end{array}C-R_2 \longrightarrow Prot\ NH-\overset{\overset{H}{|}}{\underset{\|}{C}}-R_2 + R_1OH$$

X denotes a functional group which is capable of reacting with a free thiol radical.

In particular, X can denote a pyrid-2-yl or pyrid-4-yl group which is optionally substituted by one or more alkyl, halogen or carboxylic acid radicals. X can also denote a phenyl group which is preferably substituted by one or more nitro or carboxylic acid groups. X can also represent an alkoxycarbonyl group, such as the methoxycarbonyl group.

The radical R denotes any radical which is capable of simultaneously carrying the substituents Y and S—S—X. The radical chosen must not contain groups which are capable of interfering, in the course of the subsequent reactions, with the reagents used and the products synthesized. In particular, the group R can be a group $-(CH_2)_n-$, in which n is between 2 and 10, or also a group $$\begin{array}{c}R_3-CH- \\ | \\ CH- \\ | \\ R_4\end{array}$$

in which $R_4$ denotes hydrogen or an alkyl group having from 1 to 8 carbon atoms, and $R_3$ denotes a substituent which is inert towards the reagents subsequently used, such as an amide group $$-NH-\underset{\underset{O}{\|}}{C}-OR_5,$$

in which $R_5$ denotes a linear or branched alkyl group having from 1 to 5 carbon atoms, in particular the tert.-butyl group.

The reaction of the compound Y—R—S—S—X with the immunoglobulin is carried out in the homogeneous liquid phase, most frequently in water or a buffer solution. When required by the solubility of the reagents, it is possible to add to the reaction medium up to 20% by volume of a water-miscible organic solvent, such as an alcohol, in particular tertiary butanol.

The reaction is carried out at ambient temperature for a time which varies from a few hours to 24 hours. Thereafter, dialysis makes it possible to remove the products of low molecular weight and, in particular, the excess reagents. This process makes it possible to introduce a number of substituent groups of between 1 and 5 per molecule of protein.

Using such compounds, the coupling with the A chain of ricin is carried out by bringing the two proteins into contact with one another in aqueous solution, at a temperature which does not exceed 30° C., for a time which varies from a few hours to one day. The reaction takes place in accordance with the equation:

Prot—R—S—S—X + ASH →
Prot—R—S—S—A + XSH in which Prot—R—S—S—X represents the substituted immunoglobulin (or its fragment), activated on the sulphur atom, and ASH represents the A chain of ricin. The solution obtained is dialysed in order to remove the products of low molecular weight, and the conjugate can then be purified by various known methods, as indicated in the first process for the preparation of the conjugates.

In the French application No. 81 21 836 there is described in addition the property of ammonium ions (in the form of any one of their salts and in particular the chloride) of effectively potentiating the cytotoxic action of these immunotoxins.

In another prior application filed in France under the No. 82 02 091, applicant describes the property of substances belonging to the class of carboxylic ionophors of potentiating the activity of the immunotoxins and of accelerating their kinetic action, according to modalities similar to those already described for ammonium ions.

All these potentiating and accelerating substances may be used to improve the effectiveness of immunotoxins, either in vitro, or in vivo in man or animal, for therapeutic purposes.

An object of the present invention is the preparation of powerful cytotoxic medicaments using the potentiation of the selective cytotoxic effects of the immunotoxins described in the abovementioned patent applications.

After numerous other substances have been studied without success, it has been found that chloroquin used in the form of any one of its pharmaceutically-acceptable salts was a particularly interesting substance for potentiating and accelerating the selective cytotoxic effect of immunotoxins. In fact, and in particular for the in vivo therapeutic applications, chloroquin possesses the advantage of having been used as a medicament in man for numerous years. Its modalities of use in therapeutics are hence very well known. It is a well-tolerated medicament up to relatively high doses (of the order of 2 g in a single dose in the adult man) and which presents particularly interesting pharmacokinetic characteristics due to slow urinary elimination, for 70 percent of the dose in unchanged form and a very long serum half-life (40 to 70 hours).

In the present invention, it has been found that, surprisingly, chloroquin used at doses where it presents itself no particular cytotoxicity for the lines studied, potentiates in an extremely-important manner (factor of 2500) the specific cytotoxicity of immunotoxins.

The following non-limiting example enables the scope of the invention to be better understood.

EXAMPLE

This example demonstrates the potentiation of the selective cytotoxicity of anti-T65 immunotoxin (as described in application No. 81 21 836 of applicant) with respect to human T lymphoblastoid cells of the CEM line bearing the T65 antigen.

Conjugate obtained by reaction between a human anticell T antibody (antibody directed against the antigen T65), substituted by an activated disulfide group and the chain A of ricin.

(a) Human anti-cell T antibody (or antibody T101)

This antibody was obtained according to the method described in the *Journal of Immunology,* 125 (2), 725–737 (1980).

It undergoes ultimate purification by dialysis against a PBS buffer (10 mM of phosphate, 140 mM of sodium chloride, pH 7.4).

(b) Chain A of ricin

The chain A ricin was prepared and purified as indicated in applicants' earlier applications (French Patent Applications Nos. 78 27838 and 79 24655).

The extraction of ricin starts by grinding the seeds of Ricinus communis to produce a paste from which the oil must be removed by means of a solvent for the lipids, for example, by repeated extractions with ethyl ether. After drying, the powder obtained is extracted cold by stirring with a solution of sodium chloride in a slightly acid medium, preferably at a temperature which does not exceed 4° C. After separating off the sediments, the extract is dialysed for a long time, first against water and then against a buffer of low ionic strength (TRIS-HC1, 10 mM, pH =7.7). A slight precipitation occurs during dialysis; the precipitate is separated off by filtration or centrifugation.

The extract thus obtained contains all the soluble proteins of the Ricinus communis seed, namely ricin, agglutinin and various other proteins. This solution can be frozen at −20° C., at which temperature it keeps for several weeks.

The preparation of pure ricin from the crude extract has already been described in the literature. In general, it involves chromatographic techniques, namely ion-exchange chromatography, chromatography on a molecular sieve, or also affinity chromatography. Most frequently, these various methods are combined with one another, giving rise to long and difficult techniques which cannot easily be applied to give large amounts of ricin. According to the invention, it is possible to obtain pure ricin by means of a single affinity chromatography operation, which makes it possible to separate the ricin successively from the foreign proteins and then from the agglutinin. To do this, the crude extract is deposited on a column of Sepharose 4B (an agar gel in the form of spherical particles, at a concentration of 4%, marketed by the Pharmacia Company) and then eluted in a sequential manner. Using a TRIS-HC1 buffer, 50 mM, pH =7.7, the proteins in the seed which are not lectins are eluted, and then, using a galactose solution having the concentration of between 0.28 and 0.56 mM, the pure ricin is obtained. Finally, using a 0.1 M galactose solution, the agglutinin is obtained. Total separation of the constituents from one another is achieved in a single chromatography operation if the volume of Sepharose 4B used is such that the total amount of protein introduced into the column does not exceed the capacity of the latter.

After this step, concentration by ultrafiltration makes it possible to easily obtain a solution of pure ricin, containing from 5 to 10 mg/ml of product, in a buffer of low ionic strength. The solution also contains a small amount of galactose (about 0.4 millimol/liter). Frozen at −20° C., this solution can keep for several weeks.

The two constituent chains of ricin can be separated after selective splitting of the single disulphide bridge which joins them. This splitting is carried out by means of a reducing agent, such as 2-mercaptoethanol or dithiothreitol, of which the concentration in the reaction medium must be at least 2%.

The separation of the two chains by methods using ion-exchange on various types of support has already been described, which methods are essentially based on the differences in the isoelectric points of the two chains. According to the invention, a process for separating the two chains A and B of ricin has been developed which utilizes not only the difference in the isoelectric points of the two chains, but also their different affinities towards the polysaccharide chromatographic supports containing galactose derivatives. The use of such supports also exhibits the advantage that they retain any possible traces of undivided ricin which could remain in the mixture.

In practice, the reducing agent (for example, 2-mercaptoethanol) is added at ambient temperature to the solution of ricin, obtained above, in the buffer of low ionic strength until a concentration of 2.5% volume/-volume is reached, and the solution is then deposited on a column, consisting of DEAE CL Sepharose 6B (a gel marketed by the Pharmacia Company and used for ion-exchange chromatography; it is prepared from Sepharose, or agar gel, by crosslinking with 2,3-dibromopropanol and removing the sulphate groups by alkaline hydrolysis and then introducing diethylaminoethyl groups; concentration 6% in the gel), in the same buffer containing the reducing agent. The two chains bind the column by means of bonds which are ionic with respect to the DEAE groups, and the B chain also becomes fixed to the Sepharose matrix by virtue of affinity.

The A chain is eluted by increasing the ionic strength and the pH, still in the presence of the reducing agent, so as to prevent any recombination of the two chains with one another (elution buffer: 0.1 M TRIS-HC1, pH=8.4, which is 0.1 M in respect of NaC1 and contains 2.5% of 2-mercaptoethanol). Under these conditions, the B chain remains totally fixed. It can be eluted by the same buffer which is 0.2 M in respect of sodium chloride and 0.1 M in respect of galactose.

A variant of the process for separating the A and B chains consists in using, for chromatography, a support on which the ion-exchange and molecular sieving phenomena occur simultaneously. Thus, using QAE Sephadex A.50 (a strong basic ion-exchanger obtained by fixing quaternary ammonium groups to Sephadex, or dextran gel, by means of ether bonds and marketed by the Pharmacia Company), the pure A chain can be eluted with the TRIS-HC1 buffer, 100 mM, pH=8.4, containing 0.5% of 2-mercaptoethanol, while the B chain is eluted with the same buffer which, in addition, is 75 mM in respect of sodium chloride.

In either case, the choice of the chromtographic support is very important and various other supports tested have not made it possible to achieve a good separation of the A chain.

The A chain obtained by one or another of these processes was shown to be pure with respect to the various analytical criteria, and does not require further purification. However, in order to effect its subsequent coupling with antibodies, it is necessary to have available fairly concentrated solutions which are free, in particular from the reducing agent. In order to do this, the solution of A chain in TRIS, obtained above, is dialysed against a 10 mM phosphate buffer, pH=6.5, and this simultaneously removes the TRIS, the sodium chloride, the 2-mercaptoethanol and the traces of galactose.

The solution thus obtained is deposited on a column of carboxymethylcellulose, and the A chain is then eluted by simultaneously increasing the concentration and the pH of the buffer from 10 mM, pH=6.5, to 125 mM, pH=7.0, the buffer being 1 mM in respect of EDTA. A fairly concentrated solution (about 5 mg/ml), which is ready for the coupling reactions, is thus obtained.

(c) Activated human anti-cell T antibody

To 0.5 ml of a solution of 14.2 mg/ml of 3-(2-pyridyl disulfanyl) propionic acid in tertiobutanol is added 0.1 ml of a solution of 42.7 mg/ml of 1-ethyl 3-(3-dimethylamino propyl) carbodiimide and the solution is left for 3 minutes at ambient temperature.

180 μl of the solution thus obtained are added to 5.6 ml of a solution of antibody at 3.6 mg/ml in the PBS buffer. Incubation is allowed to continue for 20 hours at 30° C.

The solution is then continuously dialysed for 3 days against 21 liters of PBS buffer at 4° C. 16 mg of activated antibody are thus obtained at a concentration of 2.6 mg/ml.

By spectrophotometric assay at 343 nm of the pyridine 2-thione released by exchange with the reduced gluthathion, it is observed that an antibody carrying 3.1 activator groups per mole of antibody is obtained.

(d) Conjugate

To 4.6 ml of a solution of activated antibody in the PBS buffer (concentration 2.6 mg/ml, or 12 mg of activated antibody) is added 0.87 ml of a solution of chain A of ricin in the same buffer (concentration 6.6 mg/ml) and incubation is carried out at 25° C. for 20 hours.

The reaction mixture is chromatographed over a Sephadex G100 gel column. In each fraction, the concentration in antibody is determined by spectrophotometry at 280 nm, and that of the chain A is determined by its power of inhibition of the proteosynthesis measured on an acellular system. The identical fractions containing the conjugate are brought together, and about 11 mg of the conjugate at the concentration of 0.8 mg/ml are obtained.

The analytical determinations made show that the solution contains 140 μg/ml of biologically active chain A, or about 1.1 mole of chain A per mole of antibody.

A study made by cytofluorometry further showed that the human anti-cell T antibody used, the corresponding activated antibody and the conjugate of this antibody with the chain A of ricin, present superposable histograms of fluorescence, which affirm that the antibody has not undergone any considerable alteration in the course of the reactions of activation and of coupling to which it was subjected, and in particular that it remains capable, within the conjugate itself, of recognizing the human antigen T against which it is directed.

In these experiments, the cytotoxicity was evaluated by the measurement of the incorporation of 14 C-leucine by the cells after 18h incubation at 37° C. in the presence of known amounts of the immunotoxin studied, or of reference cytotoxic substances, in the absence or in the presence of chloroquin.

(1) Potentiation of the cytotoxic effect by chloroquin.

The results of these experiments are presented in the form of dose effect curves having as ordinate the cytotoxic effect evaluated as indicated above by the incorporation of the tracer, calculated in percent of the value obtained on control cells without cytotoxic substance and as abscissae the molar concentrations in toxic subunits of the cytotoxic substances studied. Chloroquin was tested at a concentration of 60 micromoles. It was previously verified that chloroquin is not spontaneously cytotoxic for the cells employed, at the concentration indicated.

FIG. 1 shows the effect of chloroquin on the cytotoxicity itself of ricin and its isolated A chain, taken as reference substances. The values of the molar concentrations (CI50) corresponding to 50% inhibition of incorporation of the tracer are indicated in Table I.

In this FIG. 1, have been reported respectively the results obtained for ricin (R), the mixture ricin and chloroquin (R-C), the A chain of ricin (A) and the mixture of the A chain of ricin with chloroquin (A-C).

TABLE I

| Substances tested | With chloroquin 60 μM | Without chloroquin |
|---|---|---|
| ricin | $1.2 \cdot 10^{-12}$ M | $1.9 \cdot 10^{-12}$ M |
| A chain | $3.5 \cdot 10^{-8}$ M | $5 \cdot 10^{-8}$ M |

These results demonstrate that there is practically no potentiating effect of chloroquin on the cytotoxicity of ricin (potentiating factor of 1.6) and the A chain (potentiating factor of 1.4).

Figure 2:
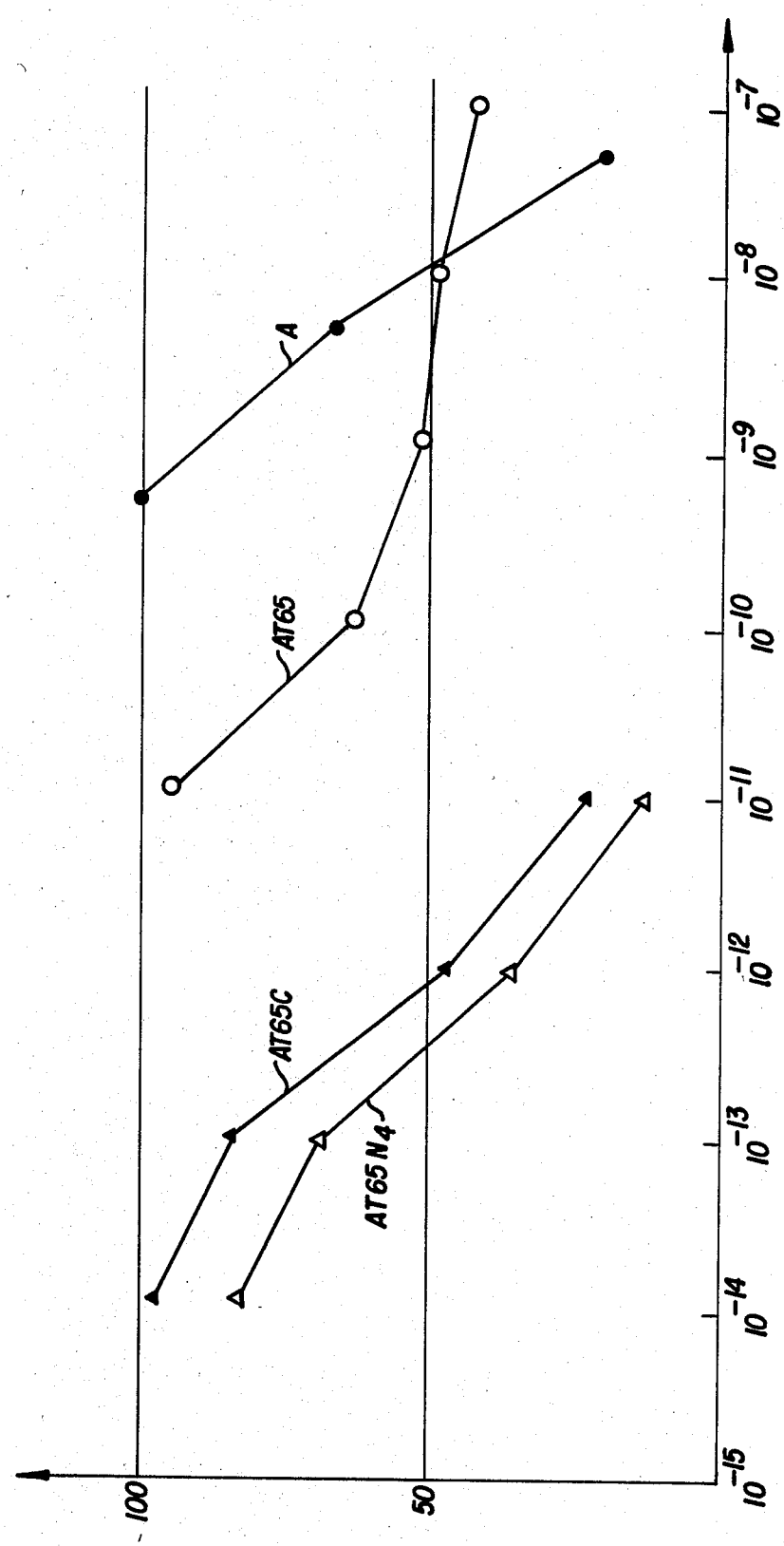

FIG. 2 shows the comparative potentiating effect of the $NH_4^+$ ion (10 mM) and of chloroquin (60 μm) on the cytotoxity of the anti-65 immunotoxin with respect to the cells of the CEM line. The values of the molar concentrations (CI50) corresponding to 50% inhibition of incorporation of the tracer are recalled in Table II.

In this FIG. 2, have been reported respectively the results obtained with the conjugate anti-T65 (AT65), the A chain of ricin (A), and the mixtures of anti-65 conjugate, with, on the one hand, a quaternary ammonium salt (AT65 Na) and, on the other hand, chloroquin (AT65 C).

These results show that the potentiating effect of chloroquin on the activity of the immunotoxin with respect to its specific target is close to that of the ammonium ion and of the order of a factor of 2,500. This signifies that in the presence of chloroquin, anti-T65 immunotoxin is with respect to its specific target a cytotoxic agent more powerful than ricin itself.

In addition, chloroquin has the remarkable property not only of potentiating the activity but also of increasing the selectivity of the immunotoxin. If one takes in fact as criterion of selectivity of action of the immunotoxin, the ratio of the CI50s of the free A chain and of the immunotoxin, this ratio is 10 in the absence of chloroquin and close to 44,000 in the presence of chloroquin.

TABLE II

| Potentiating substances tested | CI50 |
|---|---|
| None | $5 \cdot 10^{-9}$ M |

TABLE II-continued

| Potentiating substances tested | CI50 |
| --- | --- |
| NH 4 10 mM | $3.10^{-13}$ M |
| chloroquin 60 μm | $8.10^{-13}$ M |

(2) Acceleration of the cytoxity kinetics by chloroquin.

Figure 3:
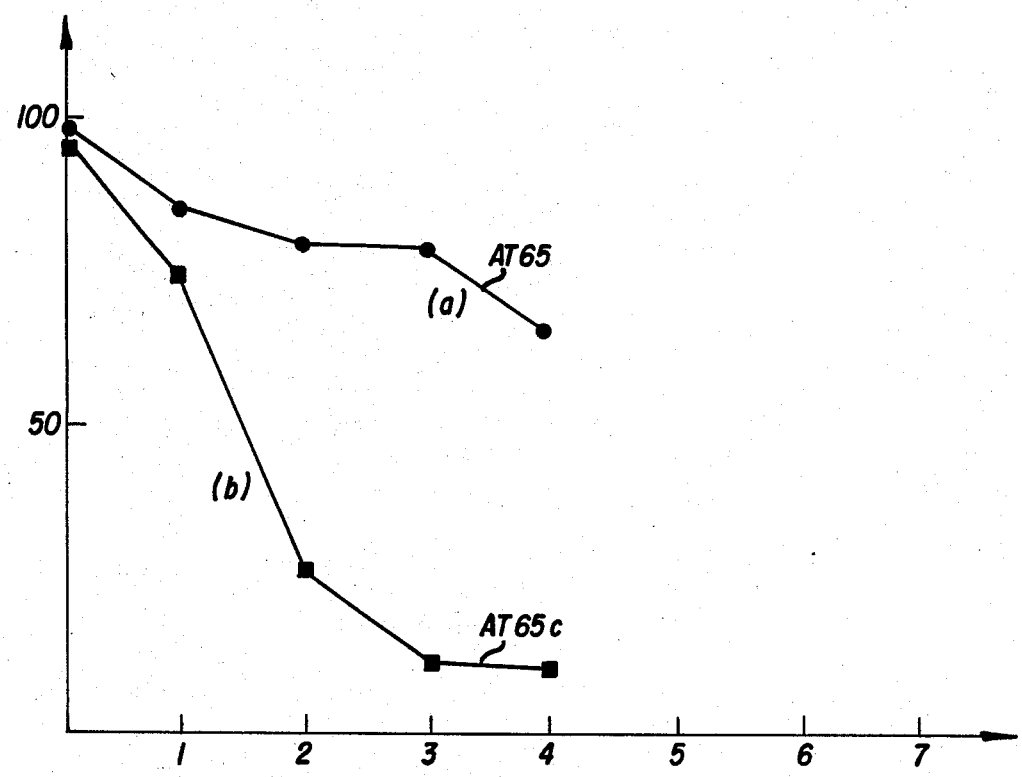

The effect of chloroquin is not limited to considerably increasing the cytotoxic activity and the selectivity of the immunotoxins. This substance also enables the acceleration in very important manner of the kinetics of cytotoxicity of the immunotoxins, as the following experiment shows:

In this experiment, there was measured as previously the incorporation of radio-active tracer in the cells but this time as a function of the incubation time of the cells with the immunotoxin, in the absence and in the presence of chloroquin 60 μm as potentiator. This experiment was carried out on the cell model constituted by the human CEM lymphoblastoid line with the anti-T65 immunotoxin at the concentration of 50 mm. The results are presented in FIG. 3.

In this Figure, there have been represented as a function of time (hours) the results obtained with the anti-T65 conjugate (AT65) and with the mixture of the anti-T65 conjugate with chloroquin (AT65 C).

For this line, it appears that in the absence of potentiation the cytotoxicity kinetics are very slow as shown by curve a. Other experiments under the same conditions have shown that the time necessary to obtain 50 percent reduction in the incorporation of the tracer was of the order of 20h. On the other hand, in the presence of chloroquin, a spectacular acceleration of the kinetics is manifested (curve b) since the time necessary to obtain 50% inhibition of incorporation is then of the order of 1.5h only.

Such an acceleration effect is of the highest importance for all immunotoxin applications and in particular for in vivo therapeutic applications since the speed of action of the medicament is always a very favorable factor in the effectiveness of the treatment.

It is hence possible to use as a medicament in human therapy the association constituted by immunotoxin and chloroquin (in the form of the base or any one of its pharmaceutically-acceptable salts). It can be used for the treatment of diseases, cancerous or not, which are sensitive to the antibody used for the preparation of the immunotoxin.

With a view to eliminating all the cancer cells, the treatment would have to be carried out with a sufficient dose of immunotoxin associated with an amount of chloroquin which can vary from 10mg to 2g (expressed as base) on each immunotoxin administration. The duration of the treatment will have to be determined in each case according to the subject and the nature of the disease to be treated.

The novel medicaments according to the invention are packaged to be usable under the conditions adapted for their use. The immunotoxin will be administered by the injectable route and preferably intravenously. The chloroquin will preferably be administered by the injectable route except if its use orally would present therapeutic advantages.

We claim:

1. A cytotoxic composition comprising a cytotoxic amount of an immunotoxin and 10 mg to 2 g of chloroquin or a pharmaceutically-acceptable salt of chloroquin, said immunotoxin comprising the A chain of ricin covalently bonded to an antibody or an antibody fragment directed against an antigen in the cell to be destroyed.

* * * * *